United States Patent [19]

Ureche

[11] Patent Number: 5,282,786
[45] Date of Patent: Feb. 1, 1994

[54] INFUSION SLEEVE FOR SURGICAL ULTRASONIC APPARATUS

[75] Inventor: Alexander Ureche, Mission Viejo, Calif.

[73] Assignee: Alcon Surgical, Inc., Fort Worth, Tex.

[21] Appl. No.: 982,278

[22] Filed: Nov. 25, 1992

Related U.S. Application Data

[63] Continuation of Ser. No. 763,722, Sep. 23, 1991, abandoned.

[51] Int. Cl.⁵ ............................................. A61B 17/20
[52] U.S. Cl. ...................................................... 604/22
[58] Field of Search ............ 128/24 AA; 604/22, 282; 606/164–171

[56] References Cited

U.S. PATENT DOCUMENTS

| | | | |
|---|---|---|---|
| 3,659,607 | 5/1972 | Banko | 604/22 |
| 4,515,583 | 5/1985 | Sorich | 604/22 |
| 4,610,674 | 9/1986 | Suzuki et al. | 604/282 |
| 4,634,420 | 1/1987 | Spinosa et al. | 604/22 |
| 4,643,717 | 2/1987 | Cook et al. | 604/22 |
| 4,702,733 | 10/1987 | Wright et al. | 604/250 |
| 4,737,153 | 4/1988 | Schimamura et al. | 604/282 |
| 4,787,889 | 11/1988 | Steppe et al. | 604/22 |
| 4,808,154 | 2/1989 | Freeman | 604/22 |
| 4,867,141 | 9/1989 | Nakada et al. | 604/22 |
| 4,869,715 | 9/1989 | Sherburne | 604/22 |
| 4,897,079 | 1/1990 | Zaleski et al. | 604/22 |
| 4,983,160 | 1/1991 | Steppe et al. | 604/22 |
| 4,988,334 | 1/1991 | Hornlein et al. | 604/22 |
| 4,989,583 | 2/1991 | Hood | 604/22 |
| 5,084,009 | 1/1992 | Mackool | 604/22 |
| 5,123,903 | 6/1992 | Quaid et al. | 604/22 |
| 5,151,084 | 9/1992 | Khek | 604/22 |

*Primary Examiner*—C. Fred Rosenbaum
*Assistant Examiner*—Michael Rafa
*Attorney, Agent, or Firm*—Jeffrey S. Schira

[57] ABSTRACT

An infusion sleeve for an ultrasonic tissue removal surgical tool includes a sleeve designed to surround the ultrasonically driven tip of the surgical tool and create an irrigation fluid channel therebetween. The sleeve includes a flexible portion which permits retraction of the distal end thereof to permit contact between the tip of the surgical tool and body tissue to be destroyed or removed. The infusion sleeve also includes a rigid portion which is designed to prevent collapse of the sleeve around the ultrasonically driven surgical tip and prevent blockage of irrigating fluid flow and subsequent overheating of the tip and damage to adjacent body tissue.

5 Claims, 2 Drawing Sheets

INFUSION SLEEVE FOR SURGICAL ULTRASONIC APPARATUS

This application is a continuation of application Ser. No. 07/763,722, filed Sep. 23, 1991 now abandoned.

FIELD OF THE INVENTION

This invention relates to an improved infusion sleeve for use with surgical apparatus employing ultrasonic means to fragment and destroy body tissue at a surgical site. The improved infusion sleeve combines flexibility to permit destruction and removal of body tissue with rigidity to prevent collapse of the infusion sleeve and damage to the wound site by overheating of the surgical tip of the ultrasonic apparatus.

BACKGROUND ART

In the prior art, a plurality of hand-held devices have been proposed for removal of body tissue during surgical procedures. One particular surgical device includes an ultrasonically driven surgical tool handpiece that destroys or emulsifies body tissue by contact between the tissue and a vibrating tip of the surgical handpiece. These types of surgical tools are used to remove a wide range of body tissue including removal of cataracts, plaque in arteries or concretions in body tissue such as kidney stones. Included with these surgical handpiece tools are means to introduce irrigation fluid to the surgical site as well as a source of aspiration or vacuum to remove destroyed or emulsified body tissue.

In certain prior art devices, the irrigation fluid is supplied to the operative tip of the surgical tool through a channel created by placement of an infusion sleeve around the operative tip assembly of the tool. U.S. Pat. No. 4,643,717 to Cook et al. discloses an ultrasonic surgical instrument utilizing these types of sleeves. The irrigating fluid supplies a medium for facilitating emulsification of body tissue and a cooling medium to prevent overheating of the vibratory tip and subsequent damage to adjacent body tissue not intended for removal.

Various materials have been utilized in prior art infusion sleeves. U.S. Pat. No. 4,787,889 to Steppe et al. discloses a flexible sleeve made of a synthetic resin such as silicon rubber which is able to fold back or telescope when inserted through an incision. Problems with these types of prior art devices include collapsing of the flexible sleeve in the area of the wound or incision site by pressure from surrounding tissue. This collapsing of the sleeve blocks flow of irrigation fluid to the surgical site and around the vibratory surgical tip causing overheating and damage to body tissue during surgery.

Other prior art devices, as described in the above-mentioned U.S. Pat. No. 4,787,889 to Steppe et al. utilize sleeves made out of metallic materials such as stainless steel. These devices do not collapse as do flexible sleeves but also are not capable of retracting away from the operative tip of the ultrasonic tip, and, therefore, are more difficult to manipulate during surgery.

As such, a need has developed to provide an improved infusion sleeve that combines flexibility and rigidity to facilitate manipulation of the surgical tool by a surgeon while protecting tissue around the wound or incision site from damage due to overheating of the surgical tool tip. In U.S. Pat. No. 4,634,420 to Spinosa et al. an infusion sleeve is disclosed which includes ribs provided around the interior circumference of the sleeve to prevent collapse when the apparatus is inserted into an eye. U.S. Pat. No. 4,983,160 to Steppe et al. discloses an infusion sleeve made of a synthetic resin material which provides sufficient rigidity to prevent collapse under the pressure of the sides of an ocular incision.

U.S. Pat. No. 4,515,583 to Sorich discloses an improved ultrasonic surgical aspirator that discloses a first sleeve configuration made of a rigid material. Alternatively, the sleeve may be made of a resilient silicon rubber material and the ultrasonic surgical tool tip is configured to provide a space between the tip and sleeve when the resilient sleeve material is compressed by the ocular incision site. U.S. Pat. No. 4,808,154 to Freeman discloses another type of infusion sleeve that is designed to prevent collapse around an ultrasonic surgical tool tip. Herein, the infusion sleeve includes a plurality of ribs on the inner surface thereof to maintain irrigation fluid flow around the vibrating surgical tool tip.

In view of the above-mentioned prior art, a need has developed to provide an improved infusion sleeve that combines flexibility and rigidity to facilitate manipulation of a surgical tool as well as prevent damage to adjacent body tissue in the area of the surgical site.

In response to this need, an improved infusion sleeve has been developed which includes a flexible portion to permit retraction away from the operative tip of an ultrasonic surgical tool and a rigid portion which prevents blockage of irrigation fluid and subsequent overheating of the ultrasonic tool as well as damage to adjacent body tissue.

SUMMARY OF THE INVENTION

It is accordingly one object of the present invention to provide an improved infusion sleeve for use with a surgical ultrasonic apparatus for removal of body tissue.

It is a further object of the present invention to provide an infusion sleeve which includes the combination of a flexible portion and a rigid portion.

It is a still further object of the present invention to provide an infusion sleeve wherein the rigid portion is configured on the sleeve to prevent collapse of the sleeve and loss of irrigation fluid supply therethrough and is adjacent a flexible portion that is retractable to permit contact of the ultrasonic apparatus with body tissue.

It is a yet further object of the present invention to provide an infusion sleeve which prevents damage to eye tissue at a surgical site by maintaining flow of irrigation fluid to an ultrasonic tip to prevent overheating thereof.

In satisfaction of the foregoing objects and advantages, there is provided an improved infusion sleeve for use with an ultrasonic tissue removal surgical tool. The improved infusion sleeve is designed to surround the tip of the ultrasonic surgical tool and provide a passageway for irrigating fluid therethrough as well as protection against damage to a wound site. The infusion sleeve includes a flexible portion which allows for retraction thereof to permit the distal end of the tip of the surgical tool to contact and remove body tissue and a rigid portion to prevent collapse of the infusion sleeve and prevent flow of irrigating fluid therethrough.

BRIEF DESCRIPTION OF THE DRAWINGS

Reference is now made to the Drawings accompanying the application wherein.

DESCRIPTION OF THE PREFERRED EMBODIMENTS

The present invention is concerned with an improved infusion sleeve for an ultrasonic tissue removal surgical tool. The infusion sleeve includes the combination of a flexible portion and a rigid portion which performs the functions of providing flexibility at the distal end of the infusion sleeve and rigidity at the site where the infusion sleeve contacts the wound to prevent collapse of the irrigating fluid channel and subsequent overheating of the ultrasonic tip. In prior art devices, infusion sleeves made of flexible or pliable material may be easily retracted when pushed against body tissue to expose the distal end of the ultrasonic tip. However, the flexible material does not have sufficient strength to prevent collapse of the sleeve around the ultrasonic tip and block the flow of irrigation fluid thereby. Without the requisite irrigation fluid flow, the ultrasonic tip overheats and causes damage to the wound site.

The improved infusion sleeve provides advantages over prior art infusion sleeves made of rigid material. Although infusion sleeves made of rigid material do not collapse at the wound site and prevent flow of irrigation fluid, the rigid material is incapable of retracting away from the distal end of the ultrasonic tip, and, therefore, complicate performance of surgical procedures.

In contrast, the infusion sleeve of the present invention provides a combination of a flexible portion which permits retraction of the sleeve away from the distal end of the ultrasonic tip as well as a rigid portion to prevent compression or collapsing of the sleeve under pressure of the tissue at the point of incision during surgery.

Figure 1:
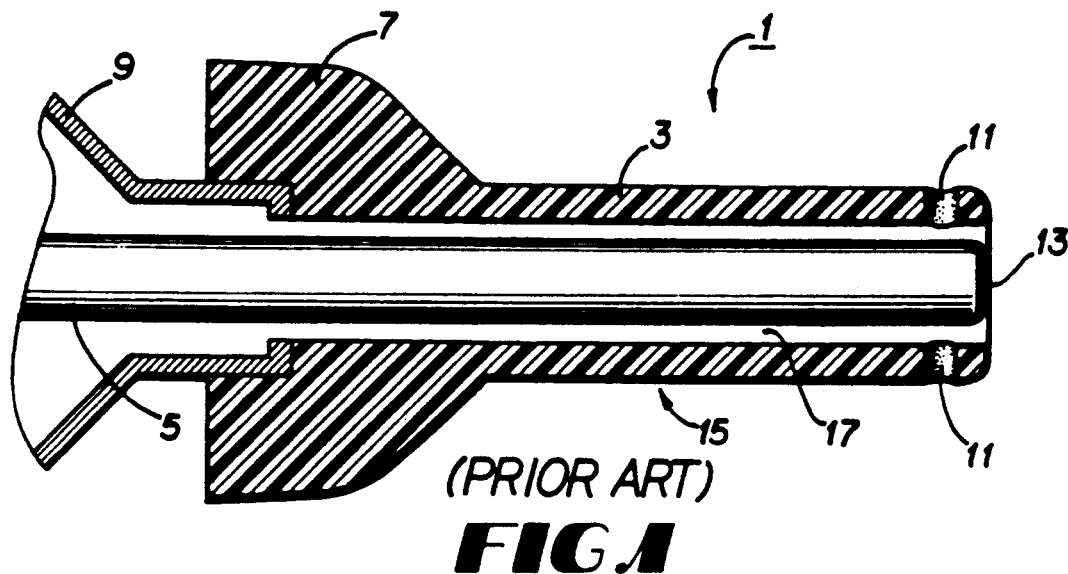
FIG. 1 is a side view partly in cross-section depicting an infusion sleeve used in prior art ultrasonic apparatus.

An example of a prior art infusion sleeve is illustrated in FIG. 1 and is generally designated by the reference numeral 1. The infusion sleeve 1 includes a tubular portion 3 which surrounds an ultrasonically driven surgical tip 5 and an enlarged portion 7 which is attached to a portion of the handle piece 9 of the surgical tool. The tubular portion 3 may have openings 11 in the distal end thereof to provide a channel for flow of irrigation fluid during use of the tool. The infusion sleeve 1 depicted in FIG. 1 is of a flexible type which permits retraction of the distal end of the sleeve away from the distal end 13 of the ultrasonically driven surgical tip 5. One of the disadvantages of these types of infusion sleeves is the tendency for the sleeve to collapse in the region 15 when contacting the tissue at the incision site where the tool has been placed therethrough and block the flow of irrigation fluid through the channel 17.

Figure 2:
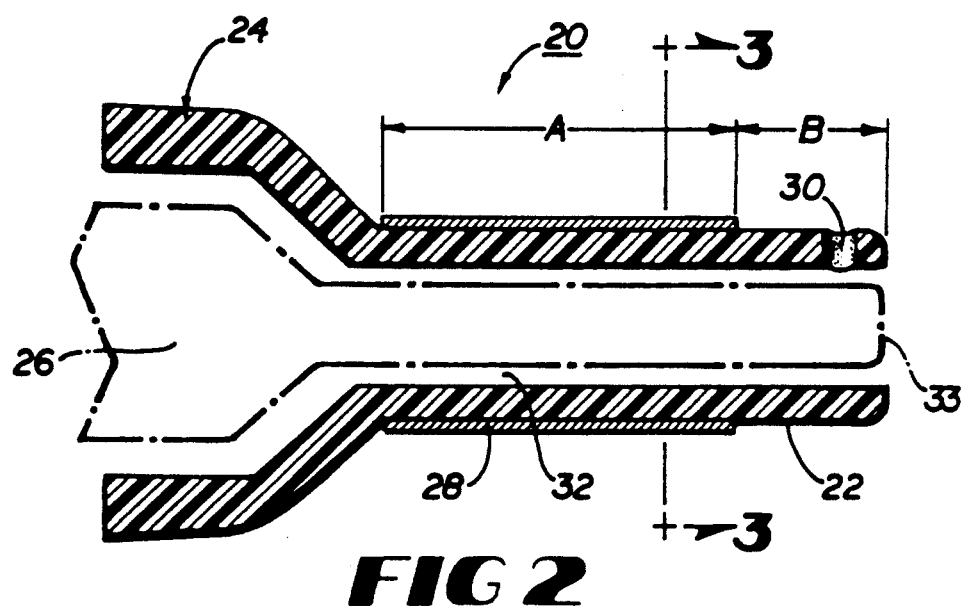
FIG. 2 shows a cross-sectional view of a first embodiment of the infusion sleeve of the present invention.

One embodiment of the infusion sleeve of the present invention is depicted in FIG. 2 and is generally designated by the reference numeral 20. The infusion sleeve 20 includes a flexible tubular portion 22 and an enlarged bore portion 24. The flexible tubular portion 22 is designed to surround an ultrasonically driven surgical tip 26 which is connected to an ultrasonic surgical tool (not shown). The infusion sleeve 20 also includes an enlarged bore portion 24 which is designed to attach to the handle (not shown) of the ultrasonic surgical tool.

The tubular member portion 22 of the sleeve 20 may also include an opening 30 or plurality of openings therethrough to facilitate flow of irrigation fluid from the surgical tool through the channel 32 to the surgical site.

The infusion sleeve 20 also includes a rigid tubular member 28 which surrounds a portion of the flexible tubular member 22. With this configuration, the distal end of the tubular member 22 can retract and permit the distal end 33 of the ultrasonically driven surgical tip 26 to contact body tissue during surgical procedures. In addition, the rigid tubular member 28 is positioned on the surface of the tubular member 22 such that the rigid tubular member 28 is in contact with the incision site made to permit passage of the surgical tool to the surgical site. The rigid tubular member 28 being in contact with the incision site prevents collapsing of the tubular member 22 and constriction of the irrigation fluid channel 32.

It should be understood that the configuration of the flexible members 22 and 24 are merely exemplary. The flexible members 22 and 24 may be configured in any design which is compatible with known ultrasonic surgical tool devices. For example, the flexible member 22 may be tapered and the enlarged bore portion 24 may include an opening therein for supply of irrigating fluid therethrough.

Figure 3:
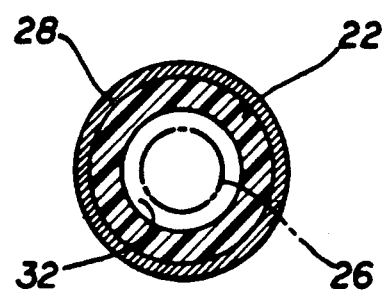
FIG. 3 shows a cross-sectional view along the line III—III depicted in FIG. 2.

FIG. 3 shows a cross-sectional view along the line III—III and more clearly illustrates the tubular configuration of the ultrasonically driven surgical tip 26, flexible member 22 and rigid member 28. The flexible members 22 and 24 may be made out of any material having sufficient flexibility to permit retraction away from the distal end 33 of the ultrasonically driven surgical tip 26. Preferred materials would include silicon. The rigid tubular member 28 may be made out of any material that would have sufficient rigidity to prevent collapse of the tubular member 22 such as metal or plastic. Preferred materials for the rigid tubular member 28 would include stainless steel or titanium. The thickness of the rigid material should be kept as small as possible so as not to interfere with the surgical procedure. A range of thickness would include from about 0.001 inches to about 0.005 inches. In addition, the rigid member 28 may be integrally attached to the flexible member 22, or alternatively, may be removably attachable by sliding over the tubular member 22 remaining in place by means of friction or other known attachment means. With reference back to FIG. 1, the rigid member 28 is seen to have a length A with the exposed tubular portion adjacent the rigid member 28 having a length B. An optimal proportion between the length of the rigid member 28, and A, the length of the exposed flexible member 22, B, would include about 3:1. However, depending upon the particular surgical application, other ratios may be utilized.

Figure 4:
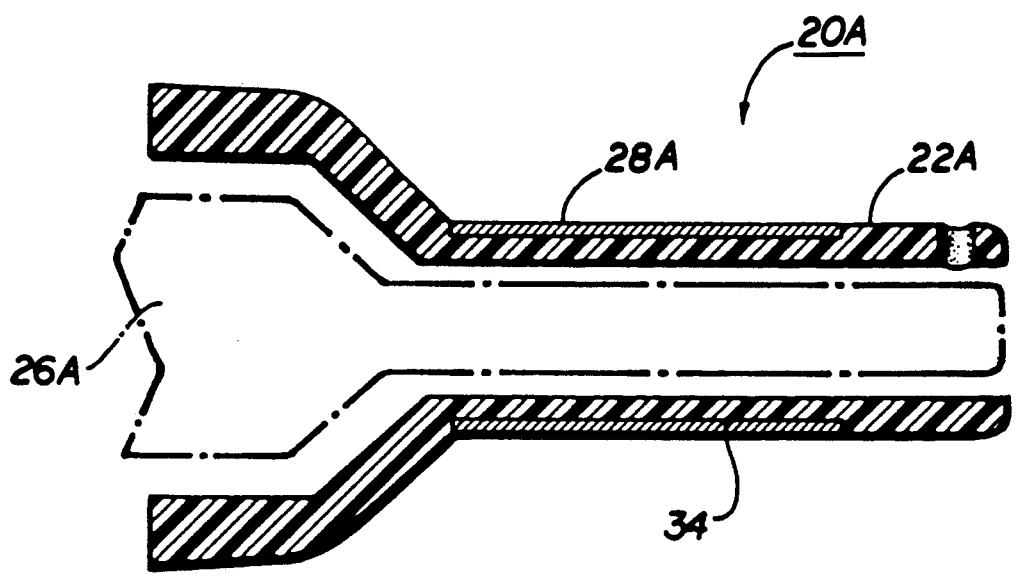
FIG. 4 shows a cross-sectional view of a further embodiment of the infusion sleeve of the present invention.

With reference to FIG. 4, a further embodiment of the infusion sleeve of the present invention is generally designated by the reference numeral 20a and is seen to include a flexible tubular member 22a having a recess 34 therein. Located within the recess 34 is a rigid tubular member 28a which functions in the same manner as that discloses for the embodiment depicted in FIG. 2. The depth of the recess 34 approximates the thickness of the rigid member 28a such that the infusion sleeve 20a has a smooth outer surface to enhance insertion and removal of the ultrasonic surgical tool through an incision site.

Figure 5:
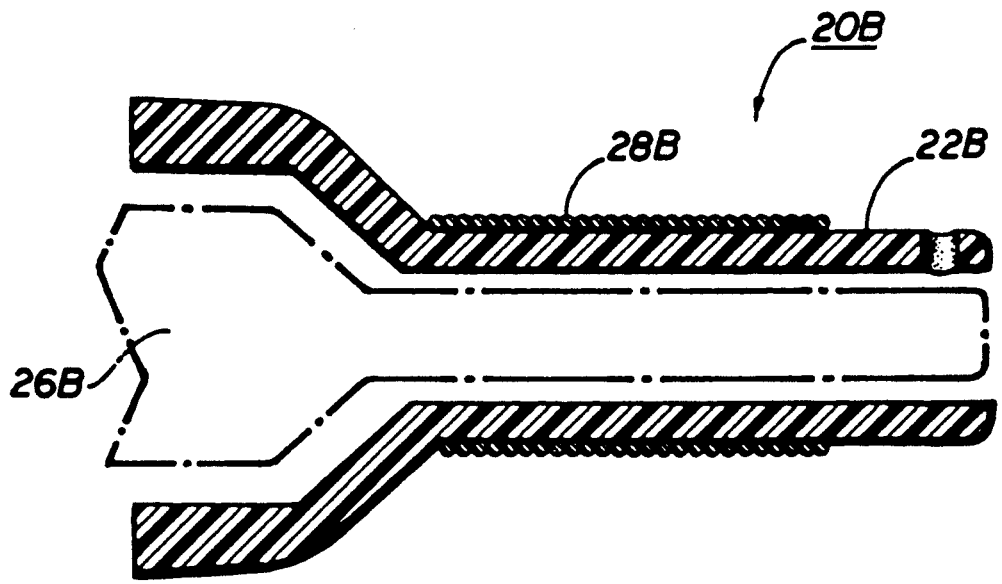
FIG. 5 shows a cross-sectional view of another embodiment of the infusion sleeve of the present invention.

FIG. 5 shows another embodiment of the infusion sleeve of the present invention which is generally designated by the reference numeral 20b. In this particular embodiment, the rigid member surrounding the rigid member 28b surrounding the flexible tubular member 22b is configured in the form of a spring. In this embodiment, the rigid member 28b provides protection against collapse of the tubular member 22b as well as longitudinal flexibility, if desired, for removal or insertion of the infusion sleeve on an ultrasonic surgical tool or for use with a ultrasonically driven surgical tip that has a curved configuration. Of course, the metal spring 28b may also be inserted into a recess in the tubular member 22b in a similar fashion as shown in the embodiment depicted in FIG. 4.

Although the infusion sleeve has been disclosed for use in any ultrasonic body tissue removing surgical tool, a preferred application of the infusion tool would include ultrasonic emulsifying handpieces for use in eye surgery. In these types of surgical applications, especially lens removal, the rigid member of the infusion sleeve provides protection against overheating of the sclera at the point of insertion into the eye. The rigid member of the infusion sleeve prevents collapse of the sleeve and blockage of the irrigation fluid channel, thus preventing overheating of the ultrasonic tip and damage to adjacent eye tissue.

As such, an invention has been disclosed in terms of preferred embodiments thereof which fulfill each and every one of the objects of the invention as set forth hereinabove and provides a new and improved infusion sleeve for ultrasonic tissue removal surgical tools of great novelty and utility.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. An infusion sleeve for use in combination with a cutting tip of a phacoemulsification handpiece, comprising:
    a) a base having an enlarged bore;
    b) a flexible tube having an external surface with a recess intersecting and connected to the base, the tube further having an open end opposite the base and a longitudinal bore in communication with the enlarged bore that receives the cutting tip; and
    c) a rigid tubular member surrounding the tube and located within the recess.

2. The infusion sleeve of claim 1 wherein the rigid tubular member comprises rigid tubing.

3. The infusion sleeve of claim 1 wherein the rigid tubular member comprises a spring.

4. The infusion sleeve of claim 1 wherein the sleeve comprises a resilient material.

5. The infusion sleeve of claim 4 wherein the resilient material comprises silicone rubber.

* * * * *